United States Patent [19]

Yamamoto et al.

[11] Patent Number: 5,466,689
[45] Date of Patent: Nov. 14, 1995

[54] MORPHOLINE DERIVATIVES AND THEIR USE

[75] Inventors: Mitsuo Yamamoto; Takayuki Doi, both of Osaka; Kaneyoshi Kato, Hyogo, all of Japan

[73] Assignee: Takeda Chemical Industries, Ltd., Osaka, Japan

[21] Appl. No.: 190,610

[22] Filed: Feb. 2, 1994

[30] Foreign Application Priority Data

Feb. 8, 1993 [JP] Japan .................................. 5-020340

[51] Int. Cl.⁶ ...................... A61K 31/535; C07D 498/06
[52] U.S. Cl. ........................... 514/229.5; 544/73; 544/99
[58] Field of Search ..................... 544/99, 73; 514/229.5

[56] References Cited

U.S. PATENT DOCUMENTS

| | | | |
|---|---|---|---|
| 4,238,486 | 12/1980 | Jones | 424/248.4 |
| 4,318,910 | 3/1982 | Nedelac et al. | 424/248.4 |
| 4,493,836 | 1/1985 | Nedelec et al. | 424/248.4 |

FOREIGN PATENT DOCUMENTS 0037784  10/1981  European Pat. Off. .

OTHER PUBLICATIONS

Jones et al., Chemical Abstracts, vol. 105, No. 19, 10 Nov., 1986, Abstract No. 164465t.

*Primary Examiner*—Richard L. Raymond
*Attorney, Agent, or Firm*—Wenderoth, Lind & Ponack

[57] ABSTRACT

A compound represented by the formula

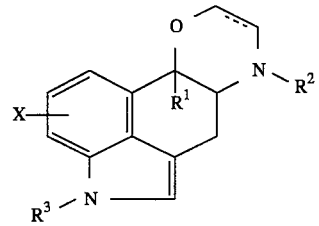

wherein X is hydrogen or a substituent; $R^1$ is an optionally substituted hydrocarbon residue; $R^2$ and $R^3$ are respectively hydrogen or a substituent; and ----- shows a single bond or a double bond, or a pharmacologically acceptable acid addition salt thereof, has an analgesic action and is useful as a medicine.

11 Claims, No Drawings

1

MORPHOLINE DERIVATIVES AND THEIR USE

FIELD OF THE INVENTION

This invention relates to novel condensed morpholine derivatives.

BACKGROUND OF THE INVENTION

Compounds having an indolobenzoxazine skeleton were disclosed in U.S. Pat. Nos. 4,493,836 and 4,318,910 by Lucien Nedelec et al., and in U.S. Pat. No. 4,238,486 by James H. Jones, in which anti-Parkinson and antihypertensive activity is indicated. In these known compounds, the carbon atom at the 1a position of the indolobenzoxazine skeleton is unsubstituted.

Pain is a complaint due to physical or mental causes, and man has endeavored, since ancient times, to synthesize drugs capable of eliminating or relieving the pain.

Stimuli causing pain include, among others, chemical, electrical, thermal and mechanical ones. Pain signals given to primary sensory nerves by these stimuli are transmitted to the cerebral cortex through the spinal cord, where the sensation is recorded as pain. In the transmission of pain, various neuropeptides participate. Above all, substance-P (SP) is a peptide consisting of 11 amino acids belonging to tachykinins, which is counted as one of the substances transmitting information from the primary sensory nerve to the dorsal horn of the spinal cord, which participates in, other than pain, central nervous system diseases and inflammatory diseases. Therefore, drugs capable of suppressing the stimuli transmitting the action of SP can be used as excellent analgesics.

As a strong analgesic which has been known best, mention is made of the narcotic analgesics, e.g. morphine, and a number of its related compounds have been synthesized. Most of these drugs, however, cause tolerance and physical and mental dependency, and the strength of such tolerance and dependency is assumed to be in direct proportion to the analgesic activity. Circumstances being such as above, the development of a non-narcotic analgesic which does not act on a morphine-acceptor has been ardently desired.

SUMMARY OF THE INVENTION

The present inventors found that novel indolobenzoxazine derivatives modified by introducing into their 1a-position a hydrocarbon residue such as lower alkyl, lower alkenyl, lower alkynyl or aryl presented analgesic actions in various animal models, and then conducted further investigation on the finding to complete the present invention.

Thus, this invention relates to: compounds (I) represented by the formula

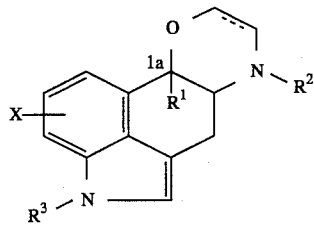

(Formula 1)

wherein X is hydrogen or a substituent; $R^1$ is an optionally substituted hydrocarbon residue; $R^2$ and $R^3$ are respectively hydrogen or a substituent; and ----- represents a single bond or a double bond, or a pharmacologically acceptable acid addition salt thereof, and the use of the compound as an analgesic.

DESCRIPTION OF THE PREFERRED EMBODIMENTS

Referring to the compound (I) above, there may be mentioned more particularly, compounds in which X represents, hydrogen, a lower alkyl, a lower alkoxy or halogen;

$R^1$ represents a lower alkyl, a lower alkenyl, a lower alkynyl or aryl;

$R^2$ represents hydrogen or an optionally substituted lower alkyl, and $R^3$ represents hydrogen or an optionally substituted lower alkyl or sulfonyl group.

Referring to the above-mentioned X, $R^1$, $R^2$ $R^3$, fluorine, chlorine, bromine and iodine are mentioned as halogen. The lower alkyl includes $C_{1-6}$ straight-chain or branched saturated hydrocarbon, one or more hydrogen atoms of which may be optionally substituted with halogen, as exemplified by methyl, ethyl, n-propyl, iso-propyl, n-butyl, iso-butyl, n-pentyl, n-hexyl, trifluoromethyl, difluoromethyl, monofluoromethyl, pentafluoroethyl and 2-trifluoroethyl.

The lower alkenyl includes $C_{2-6}$ straight-chain or branched unsaturated hydrocarbon having a double bond in the molecule, as exemplified by vinyl, allyl, 2-propenyl, 2-butenyl, isoprenyl, 2-pentenyl, 3-pentenyl, 4-pentenyl, 2-hexenyl, 3-hexenyl, 4-hexenyl and 5-hexenyl.

The lower alkynyl includes $C_{2-6}$ straight-chain or branched unsaturated hydrocarbon having a triple bond in the molecule, as exemplified by propargyl, ethynyl, 2-propynyl, 3-propynyl, 1-hexynyl, 2-hexynyl, 3-hexynyl and 4-hexynyl.

The lower alkoxy includes functional groups formed by binding the above-mentioned lower alkyl through oxygen atom, as exemplified by $C_{1-6}$ alkoxy such as methoxy, ethoxy, n-propoxy, n-butoxy, t-butoxy, isopropoxy and trifluoromethoxy.

The aryl includes monocyclic or condensed polycyclic aromatic hydrocarbon, as exemplified by phenyl, naphthyl, indenyl and anthryl.

As substituents for the optionally substituted lower alkyl group shown by the above-mentioned $R^2$, mention is made of, for example, the above-mentioned halogen atoms, aryl or cycloalkyl, heterocyclic ring, aralkyl and acyl. The aryl and heterocyclic ring may optionally be substituted on the lower alkyl through an oxygen, sulfur or nitrogen atom.

The cycloalkyl includes 3- to 7-membered ring formed with solely carbon atoms, which may optionally have a double bond in the molecule, as exemplified by cyclopropyl, cyclobutyl, cyclopentyl, cyclohexyl, 2-cyclohexen-1-yl and 2-cyclopenten-1-yl.

The heterocyclic ring includes rings which may be 4- to 7-membered monocyclic or condensed cyclic rings optionally having unsaturated bonds and having at least one oxygen atom, nitrogen atom, and sulfur atom as the ring-constituting atoms, as exemplified by 2-thienyl, 3-thienyl, 2-pyridyl, 3-pyridyl, 4-pyridyl, 2-furyl, 3-furyl, 4-quinolyl, 8-quinolyl, 4-isoquinolyl, pyrazinyl, 2-pyrimidinyl, 1-pyrrolidinyl, 2-pyrrolidinyl, 3-pyrrolidinyl, 2-imidazolinyl, 3-imidazolinyl, 1-piperidyl, 3-piperidyl, 1-morpholinyl, 2-morpholinyl, 3-morpholinyl, 4-morpholinyl, 1-piperazinyl, 2-piperazinyl, 3-piperazinyl, 2-isoindolinyl and 1-phthalimide.

The aralkyl includes functional groups formed by binding one or more aryl groups through lower alkyl, as exemplified by benzyl, phenylethyl, diphenylmethyl, triphenylmethyl, 1-naphthylmethyl, 2-naphthylmethyl, 2-diphenylethyl, 3-phenylpropyl, 4-phenylbutyl and 5-phenylpentyl.

The acyl includes functional groups formed by binding the above-mentioned lower alkyl, lower alkenyl, lower alkynyl, aryl, cycloalkyl, aralkyl or heterocyclic ring through carbonyl, phosphoryl or sulfonyl, as exemplified by formyl, acetyl, propionyl, butyryl, valeryl, acryloyl, propiolyl, benzoyl, nicotinoyl, methanesulfonyl, ethanesulfonyl, benzenesulfonyl, toluenesulfonyl and 2,4,6-triisopropylbenzenesulfonyl.

The above-mentioned aryl, aralkyl and heterocyclic ring may optionally have, at optional positions, one or more substituents which may be the same or different from one another.

The optional substituents include the above-mentioned lower alkyl, lower alkenyl, lower alkynyl, cycloalkyl or cyano, nitro, sulfonyl, amino, lower monoalkylamino, lower dialkylamino, arylamino, hydroxyl group, lower alkoxy, halogen, carbamoyl, carboxyl, lower alkoxycarbonyl, lower alkanoyl, mercapto, lower alkylthio, aralkyl (e.g. benzyl), aryl (e.g. phenyl), lower alkyl carbamoyl, arylcarbamoyl (e.g. phenylcarbamoyl), acyl (e.g. benzoyl, nicotinoyl), methylenedioxy, heterocyclic ring (preferably 4-pyridyl, 2-pyridyl, 3-pyridyl and 2-pyrimidinyl), or the like.

Among the compounds (I), preferable ones are those wherein X stands for hydrogen; $R^1$ stands for a lower alkyl, a lower alkenyl or phenyl; $R^2$ stands for hydrogen, a lower alkyl or a group (II) shown by the formula, —$(CH_2)_nAR^4$ (Formula 2): wherein n is an integer of 1 to 6, A is a bond or oxygen, sulfur or nitrogen atom, $R^4$ is hydrogen, phenyl, 1-phthalimidyl or 4-benzylpiperazyl; $R^3$ stands for hydrogen, 2,4,6-triisopropylbenzenesulfonyl or p-toluenesulfonyl and ----- represents a single bond.

Examples of pharmacologically acceptable acid addition salts include inorganic salts such as hydrochloride, hydrobromide, hydroiodide, sulfate or phosphate, and organic salts such as acetate, oxalate, succinate, ascorbate, maleate, lactate, citrate, fumalate, tartrate, methanesulfonate or benzoate.

It is preferable that the compounds (I) of this invention have the following steric configuration;

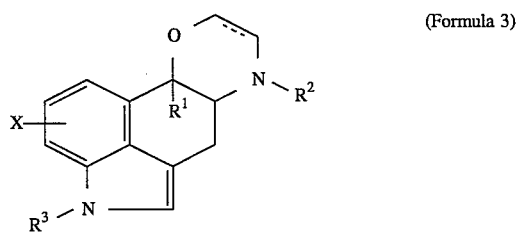

(Formula 3)

wherein X, $R^1$, $R^2$ and $R^3$ have the same meaning as defined above.

Further, in the compounds included in the present invention, there exist optical isomers, and the optically active compounds obtained by optical resolution of those isomers are also included in the present invention.

The compounds (I) of this invention can be produced by, for example, subjecting a compound (IV) of the formula

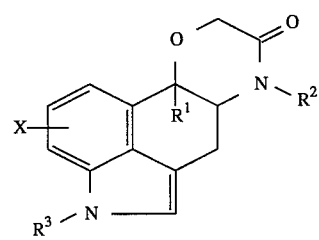

(Formula 4)

wherein X, $R^1$, $R^2$ and $R^3$ are as defined above to reduction, and, when desired, by further subjecting the reduced compound to reduction, oxidation or/and substitution reaction.

The above-mentioned reduction is conducted in an inert solvent by reacting with a metal hydride (e.g. lithium aluminum hydride, lithium boron hydride, sodium cyano borohydride or diborane). As the inert solvent, mention is made of ether (e.g. ethyl ether, tetrahydrofuran or dioxane), halogenated hydrocarbon (chloroform, dichloromethane), hexane, benzene, toluene or the like. The metal hydride is used in an amount of 1 to 20 equivalents, preferably 3 to 12 equivalents, and the reaction temperature ranges from –70° C. to 50° C. Preferably, the reaction is conducted in an ether solvent at temperatures ranging from 0° C. to 30° C. with lithium aluminum hydride.

Further, introduction and modification of substituents can be conducted, for example, in the following manner.

The alkylation on the secondary nitrogen atom is conducted with a base (1 to 5 equivalents, preferably 2 to 3 equivalents) in an inert solvent, for example, water, ether (e.g. tetrahydrofuran, ethyl ether or dioxane), acetonitrile, N,N-dimethylformamide and halogenated hydrocarbon, singly or a mixture of them. Examples of the base include potassium carbonate, sodium carbonate, sodium hydride, potassium hydride, sodium ethoxide and potassium-t-butoxide, and the reaction temperature ranges from –50° C. to 80° C., preferably from 0° C. to 30° C.

The acylation on the secondary nitrogen atom is conducted by allowing a reactive derivative of chlorine, acetic acid or bromoacetic acid (e.g. chloroacetyl chloride, bromoacetyl bromide or bromoacetyl chloride) to react in an inert solvent. Preferable examples of the inert solvent include water, ether, halogenated hydrocarbon, acetonitrile and N,N-dimethylformamide, and they are used singly or as a mixture. Depending on the specific case, a base is added to the reaction system, as exemplified by inorganic bases (sodium carbonate, sodium hydrogencarbonate, sodium hydroxide, potassium carbonate, etc.) or organic bases (triethylamine, pyridine, 4,4-dimethylamino pyridine, diisopropyl ethylamine, etc.). The amount of the base ranges from 1 to 10 equivalents, preferably from 1 to 3 equivalents. The reaction temperature ranges from 0° C. to 50° C., preferably from 10° C. to 30° C.

The elimination of a base shown by $R^3$ (e.g. sulfonyl derivatives) can be conducted by basic hydrolysis, acid hydrolysis or reductive elimination, and the last one is preferable. The reaction is conducted by processing with sodium naphthalene prepared from metallic sodium and naphthalene or a metal hydride (e.g. lithium aluminum hydride) in an inert solvent (e.g. ether, toluene or hexane, singly or as a mixture). The amount of the reducing agent ranges desirably from 5 to 20 equivalents. As the inert solvent, tetrahydrofuran is preferably employed, and the reaction temperature ranges from 0° C. to 40° C., preferably around room temperature.

The starting compound (Formula 4) can be produced from 3,4-dihydrobenzo[cd]indol-5(1H)-one (J. Chem. Soc., p.1438, 1973) or a derivative thereof by the following steps in accordance with the method described by Bowman (J. Chem. Soc., p.1121, 1972).

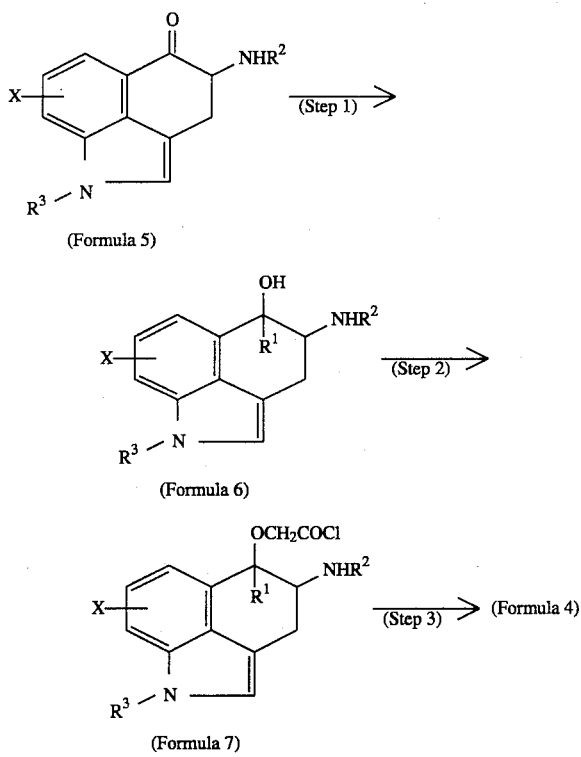

wherein X, $R^1$, $R^2$ and $R^3$ are of the same meaning as defined above.

Step 1

This step is a nucleophilic addition reaction on the ketone group. The reaction is conducted by reacting with an organometallic reagent represented by $R^1$-M (M stands for Li, Na, MgBr, MgCl or $CeCl_2$) in an inert solvent. As the inert solvent, use is made of tetrahydrofuran, ethyl ether, dimethoxyethane or dioxane, singly or as a mixture. The amount of the organometal ranges from 1 to 20 equivalents, preferably from 4 to 10 equivalents. The reaction temperature ranges from −100° C. to 70° C., preferably from −20° C. to 25° C.

Step 2

This is a chloroacetylation reaction, which is conducted in accordance with the method of Lucien Nedelec et al. (JP-A-133292/1981). Namely, the reaction with chloroacetyl chloride (preferably 1 to 2 equivalents) is conducted in an inert solvent in the presence of an excess amount of a base. As the inert solvent, use is made of water, ether (ethyl ether, tetrahydrofuran or dioxane), halogenated hydrocarbon (chloroform, dichloromethane or dichloroethane), ethyl acetate, acetonitrile and N,N-dimethylformamide, singly or as a mixture. The reaction is conducted at temperatures ranging from 0° C. to 50° C. Preferable bases are exemplified by potassium carbonate, sodium carbonate, sodium hydroxide and potassium hydroxide, and, preferable inert solvents include tetrahydrofuran, chloroform and dichloromethane. Preferable reaction temperatures range from 0° C. to 30° C.

Step 3

This is intramolecular cyclization. The reaction is conducted by processing with a base (1 to 5 equivalents, preferably 2 to 3 equivalents) in an inert solvent, for example, ether (e.g. tetrahydrofuran, ethyl ether or dioxane), acetonitrile, N,N-dimethylformamide or halogenated hydrocarbon, singly or as a mixture. Preferable examples of the base include inorganic strong bases (e.g. sodium hydride, potassium hydride, sodium hydroxide, potassium hydroxide, sodium ethoxide or potassium-t-butoxide), an especially preferable one being sodium hydride. Preferable examples of the inert solvent include tetrahydrofuran, acetonitrile and N,N-dimethylformamide, which can be used singly or as a mixture. The reaction temperatures range preferably from 0° C. to 40° C.

Optically active compounds can be produced by per se known means, more specifically stating, by using an optically active synthetic intermediate or by subjecting the mixture of the ultimate racemic compounds to optical resolution.

As the optical resolution, mention is made of a method which comprises allowing an optically active acid and salt to be formed, followed by separating them by fractional recrystallization; a method which comprises subjecting a racemic compound or a salt thereof to chromatography using a column for separation of optically active compounds (chiral column), for example, ENANTIO-OVM (Toso Co., Ltd.), followed by developing with a solvent such as water, various buffers (e.g. phosphate buffer), alcoholic solvents (e.g. methanol or ethanol), nitrile type solvents (e.g. acetonitrile), hexane or ethyl ether, singly or as a mixture; and a method which comprises subjecting a mixture of racemic compounds to condensation, by a conventional method (e.g. acid chloride method), with, for example, MPTA (α-methoxy-α-(trifluoromethyl)phenylacetic acid or menthoxyacetic acid to give a mixture of diastereomers of amido-compound, which is subjected to separation and purification by means of fractional recrystallization or a silica gel chromatography, followed by subjecting the separated and purified product to acid hydrolysis or basic hydrolysis.

The compounds (Formula 1) of this invention are antagonistic against symptoms of pain or the like induced by Substance-P, and show analgesic activity in animals.

The toxicity of the compounds of this invention is low (acute toxicity ($LD_{50}$), when Compound 2 of the Examples is orally administered to rats, is not less than 100 mg/kg) with less undesirable side effects. Therefore, the compounds of this invention and their salts can be used for prophylaxis or therapy of diseases including pain due to bone diseases (arthritis, rheumatic fever, osteoporosis), pain induced by cancer or the like, lumbago, postoperative pain, neuralgia, pain induced by inflammatory diseases, pain caused by tooth extraction, tooth-ache and pain due to burn trauma, as well as neurosis (e.g. anxiety neurosis, depression, mental disorder), somnipathy or the like. Since the compounds of this invention act on a neurotransmitting system such as dopamine or norepinephrine, they can be used also as prophylactic and therapeutic drugs for circulatory diseases (e.g. hypertension).

The compounds of this invention and their salts can be safely administered orally or non-orally as they are or as pharmaceutical compositions by being admixed with a pharmaceutically acceptable carrier, vehicle or diluent, e.g. tablets (including sugar-coated tablets, film-coated tablets), powders, granules, capsules (including soft capsules), liquids, injections, suppositories and sustained-release drugs.

While the dosage of the compounds and their salts of this invention varies with, for example, the subjects, administration routes and diseases to be treated, it ranges conveniently from 0.1 to 500 mg, preferably 1 to 100 mg, in the case of oral administration to a human adult as an analgesic agent.

EXAMPLES

In the following, Na₂SO₄ means sodium sulfate, LAH means lithium aluminum hydride, THF means tetrahydrofuran, NH₄Cl means ammonium chloride, DCE means 1,2-dichloroethane, KBr means potassium bromide, DMF means N,N-dimethylformamide and CDCl₃ means deuterochloroform.

Reference Example 1

3-(5-Methoxy-1-p-toluenesulfonylindol-3-yl)propionic acid

In THF(640 ml)-DMF(130 ml) was dissolved ethyl 3-(5-methoxy-1H-indol-3-yl)propionic acid (99.3 g, 0.4 mol). To the solution was added in limited amounts, under ice-cooling, a suspension of 60% sodium hydride in oil (18.4 g, 0.46 mol) in THF(50 ml)-DMF(10 ml). The mixture was stirred at room temperature for one hour, and the mixture was again cooled with ice. To the mixture was gradually added p-toluenesulfonyl chloride (83.9 g, 0.44 mmol), followed by stirring for a further 3 hours at room temperature. The reaction mixture was poured into an ice-saturated NH₄Cl solution (180 ml). The upper layer was subjected to extraction with ethyl acetate (100 ml+500 ml). The extract solution was washed with a saturated aqueous saline solution (300 ml×2), followed by drying over Na₂SO₄. The residue was purified by means of silica gel chromatography (eluent: hexane-ethyl acetate (2:1)) and then were added hydrochloric acid (100 ml) and acetic acid (400 ml), and was refluxed for 1 hour. The reaction mixture was concentrated and the resulting crystals were washed with water, dried under reduced pressure and washed with methanol-isopropyl ether (1:3) to obtain the title compound (54.1 g: m.p. 172°–174° C.)

Reference Example 2

3,4-Dihydro-6-hydroxy-I-p-toluenesulfonylbenz[cd]indol-5(1H)-one

To a DCE (600 ml) solution of 3-(5-methoxy-1-p-toluenesulfonyl-indol-3-yl)propionic acid (28.9 g, 77 mmol) was added, while stirring under ice-cooling, (COCl)₂ (8.3 ml, 95 mmol), and the mixture was stirred for about 2.5 hours at room temperature. The reaction mixture was concentrated, and the residue was dissolved in DCE (100 ml). The solution was added to a suspension of aluminum chloride powder (33.9 g, 254 mmol) in DCE (430 ml) at 5° C. taking 20 minutes. The mixture was left standing as it was at 5° C. for one hour, then stirred for 2.5 hours at room temperature. To the reaction mixture were added, under ice-cooling, dimethoxyethane (300 ml) and water (300 ml). Resulting precipitates were filtered off, then the organic layer was separated. The aqueous layer was subjected to extraction with chloroform (200 ml). The extract solution was combined with the organic layer, which was washed with an aqueous saline solution. The resultant organic layer was dried (anhydrous sodium sulfate), then the solvent was distilled off under reduced pressure to leave 25 g of crude crystals. The crude crystalline product was subjected to silica gel column chromatography, eluting with chloroform, to obtain crystals, followed by recrystallization from chloroform-n-hexane to afford the title compound (m.p.210°–211° C.).

¹H-NMR(CDCl₃, 200 MHz) δ: 2.36(s,3H), 2.81(t,J=7Hz, 2H), 3.13(t,J=7 Hz,2H), 6.8–8.0(m,7H) ppm. IR(KBr): 3095, 1643 cm⁻¹. Anal: Calcd. for $C_{18}H_{15}NO_4S$; C 63.33%, H 4.43%, N 4.10% Found: C 63.22%, H, 4.39%, N 4.08%.

Reference Example 3

3,4-Dihydro-6-methoxy-1-p-toluenesulfonylbenz[cd]indol-5(1H)-one

To a solution of the crude crystals (42 g) obtained in Reference Example 2 in N,N-dimethylformamide (400 ml) were added potassium carbonate (60.7 g, 440 mmol) and methyl iodide (39.7 g, 280 mmol). The mixture was stirred for about one hour at room temperature, and to the mixture were further added potassium carbonate (20.0 g, 140 mmol) and methyl iodide (15.0 g, 110 mmol). The mixture was stirred for an additional one hour at room temperature. To the reaction mixture was then added water (1000 ml), which was subjected to extraction with ethyl acetate (400 ml×2). The extract solution was washed with an aqueous saline solution and dried (anhydrous Na₂SO₄). The solvent was then distilled off under reduced pressure. The residue was subjected to silica gel column chromatography, eluting with n-hexane-ethyl acetate (1:1) to afford the title compound (48%).

¹H-NMR(CDCl₃, 200 MHz) δ: 2.36(s,3H), 2.78(t,J=7 Hz,2H), 3.10(t,J=7 Hz,2H), 3.96(s,3H), 6.9–8.1(m,7H), ppm. IR(KBr): 2940, 1682 cm⁻¹. Anal: Calcd. for $C_{19}H_{17}NO_4S$; C 64.21%, H 4.82%, N 3.94% Found: C 63.54%, H 4.97%, N 3.93%

Reference Example 4

4-Azido-3,4-dihydro-6-methoxy-1-p-toluenesulfonylbenz[cd]indol-5(1H)-one

To a solution of 3,4-dihydro-6-methoxy-1-p-toluene sulfonylbenz[cd]indol-5(1H)-one (5.1 g, 14.3 mmol) in THF (60 ml) was gradually added, under stirring at −45° C., a solution of Me₃PhNBr₃ (5.38 g 14.3 mmol) in THF (20 ml), and the mixture was warmed up to 10° C. After completion of the reaction, insolubles were filtered off. The filtrate was subjected to distillation under reduced pressure to leave 7.5 g(100%) of 3,4-dihydro-4-bromo-1-(p-toluenesulfonyl)benz[cd]indol-5-one as crude crystals. Then, this crude crystalline product was dissolved in N,N-dimethylformamide-acetic acid (140 ml-2 ml). To the solution was gradually added, under stirring at −28° C., an aqueous solution (14 ml) of sodium azide (1.86 g, 28.6 mmol) to raise the temperature to about 0° C. After completion of the reaction, the reaction mixture was added to ice-water (300 ml). Resulting crystalline precipitates were collected by filtration and, then dissolved in ethyl acetate, and the solution was shaken to make two layers. The organic layer was washed with an aqueous saline solution and dried (anhydrous Na₂SO₄). The solvent was then distilled off under reduced pressure to leave 5.67 g (100%) of the title compound as crude crystals. A portion of the crystalline product was recrystallized from ethyl acetate to afford the product, m.p.147°–148° C.

¹H-NMR(CDCl₃, 200 MHz) δ2.36(s,3H), 3.02(ddd,J=20 12, 2 Hz, 1H), 3.33(dd,J=20, 7 Hz,1H), 4.00(s,3H), 4.35(dd, J=12, 7 Hz, 1H), 6.9–8.1(m,7H) ppm. IR(KBr): 2104, 1688 cm⁻¹. Anal: Calcd for $C_{19}H_{16}N_4O_4S \cdot 0.3H_2O$; C 56.78%, H 3.83%, N 13.82%% Found: C 57.03%, H 3.91%, N 13.42%.

Reference Example 5

4-Acetylamino-3,4-dihydro-6-methoxy-1-p-toluenesulfonylbenz[cd]indol(1H)-one To a solution of 4-azido-3,4-dihydro-6-methoxy-1-p-toluenesulfonyl-5(1H)-one (5.36 g, 13.5 mmol) in THF (130 ml) were added acetic anhydride (2.76 g, 27.0 mmol) and 10% palladium-carbon (2.2 g). The mixture was stirred for 10 hours at room temperature under hydrogen atmosphere of 3 atmospheres pressure. After completion of the reaction, the catalyst was filtered off. The filtrate was subjected to distillation under reduced pressure. The residue was washed with ethyl ether to give 5.03 g (90%) of the title compound as a crude crystalline product. A portion of the product was recrystallized from chloroform-n-hexane to afford a pure product (m.p.214°–217° C.).

$^1$H-NMR(CDCl$_3$, 200 MHz) δ: 2.37(s,3H), 2.73(ddd,J=18, 14, 2, 1H), 3.85(dd,J=18, 10, 1H), 3.96(s,3H), 4.73(ddd, J=14, 10, 6, 1H), 6.78(br d, 1H), 6.9– 8.1(m,7H) ppm. IR(KBr): 3340, 1682, 1634 cm$^{-1}$. Anal: Calcd for C$_{21}$H$_{20}$N$_2$O$_5$S.1.0H$_2$O: C 58.59%, N 6.51% Found; C 59.02%, H 4.88%, N 6.42%.

Reference Example 6

4-Amino-3,4-dihydro-6-methoxy-1-p-toluenesulfonylbenz [cd]indol-5(1H)-one hydrochloride To a suspension of 4-azido-3,4-dihydro-6-methoxy-1-p-toluenesulfonylbenz[cd]indol-5(1H)-one (2.0 g, 5.0 mmol) in ethanol (100 mmol) were added conc. hydrochloric acid (2.5 ml) and 10% palladium-carbon (400 mg). The mixture was stirred for 4 hours at room temperature under hydrogen atmosphere of 3 atmospheres pressure. After completion of the reaction, the catalyst was filtered off. The filtrate was subjected to distillation, and the residue was washed with ethyl ether to give 1.6 g (80%) of crude crystals of the title compound.

$^1$H-NMR(DMSO-d$_6$, 200 MHz) δ: 3.12(t,J=10 Hz, 1H), 3.89(s,3H), 4.44(m,1H), 7.2–8.1(m,7H), 8.50(br s,2H) ppm. IR(KBr): 1687 cm$^{-1}$. Anal: Calcd. for C$_{19}$H$_{19}$N$_2$O$_4$SCl.3.0H$_2$O; C 49.51%, H 5.47%, N 6.08% Found: C 49.57%, H 5.22%, N 5.95%.

Reference Example 7

3,4-Dihydro-6-methoxy-1-p-toluenesulfonyl-4-trifluoroacetylaminobenz[cd]indol-5(1H)-one To a suspension of 4-amino-3,4-dihydro-6-methoxy-1-p-toluenesulfonylbenz[cd]indol-5(1H)-one hydrochloride (1.45 g, 3.50 mmol) in dichloromethane (30 ml) were added, while stirring under ice-cooling, anhydrous trifluoroacetic acid (0.61 ml, 4.27 mmol) and triethylamine (1.18 ml, 16.1 mmol). The mixture was stirred for 30 minutes as it was. After completion of the reaction, the reaction mixture was subjected to distillation under reduced pressure. The residue was shaken together with ethyl acetate (40 ml)-1N HCl (30 ml) to allow two layers to be formed. The organic layer was washed with an aqueous saline solution and dried (anhydrous Na$_2$SO$_4$). The solvent was distilled off under reduced pressure. The residue was recrystallized from ethyl acetate-n-hexane to afford the title compound (1.2 g, 73%, m.p.189°–190° C.)

$^1$H-NMR(CDCl$_3$), 200 MHz) δ: 2.84(ddd,J=14,13,2 Hz,1H), 3.98(s,3H), 4.70(m, 1H), 7.0–8.2(m,7H) ppm. IR(KBr): 3355, 1732, 1690 cm$^{-1}$. Anal: calcd. for C$_{21}$H$_{17}$N$_2$O$_5$SF$_3$.0.5H$_2$O; C 53.05%, H 3.82%, N 5.89% Found; C 52.96%, H 3.97%, N 5.80%.

Reference Example 8

Methyl 1-(2,4,6-triisopropylphenylsulfonyl)-indole-3-propionate

Sodium hydride (60% oil 19.03 g 0.476 mol) was washed with n-hexane, and was suspended in DMF (500 ml). To the suspension was gradually added a solution of ethyl indole-3-propionate acid (64.79 g 0.317 mol) in DMF(100 ml). The mixture was stirred for one hour at 40°–50° C., and to the mixture was gradually added, under ice-cooling, 2,4,6-triisopropylphenylsulfonyl chloride (115.25 g, 0.38 mol), followed by stirring for one hour at room temperature. To the reaction mixture was added water (150 ml), and the mixture was subjected to extraction with n-hexane (500 ml). The extract solution was washed with water (100 ml) and dried over anhydrous magnesium sulfate. The solvent was distilled off under reduced pressure to to leave the title compound (152 g).

$^1$H-NMR(CDCl$_3$, 200 MHz) δ: 1.09(d,J=7 Hz,12H), 1.24(d, J=7 Hz,6H), 2.69(t,J=7 Hz,2H), 2.90(hep,J=7 Hz,1H), 3.04(t,J=7 Hz,2H), 3.65(s,3H), 4.16(hep,J=7 Hz,2H), 7.2–7.6(m,7H) ppm. IR(KBr): 2960, 1740 cm$^-$.

Reference Example 9

1-(2,4,6-Triisopropylphenylsulfonyl)-indole-3-propionic acid

In acetic acid (200 ml) was dissolved methyl 1-(2,4,6-triisopropylphenylsulfonyl)-indole propionate (152 g). To the solution was added conc. hydrochloric acid (150 ml), and the mixture was refluxed under heating for two hours. The reaction mixture was concentrated under reduced pressure, and was added to a saturated aqueous solution of sodium hydrogencarbonate to render the pH to 5–6, followed by extraction with dichloromethane (1000 ml). The extract solution was washed with water (500 ml) and dried over anhydrous magnesium sulfate. The solvent was distilled off under reduced pressure to leave the title compound (153 g) as an oily product.

$^1$H-NMR(CDCl$_3$, 200 MHz) δ: 1.09(d,J=7 Hz,12H), 1.24(d,J=7 Hz,6H), 2.76(t,J=7 Hz,2H), 2.90(hep,J=7 Hz,1H), 3.06(t,J=7 Hz,2H), 4.16(hep,J=7 Hz,2H), 7.2–7.6(m,7H) ppm. IR(KBr): 2955, 1712 cm$^{-1}$.

Reference Example 10

3,4-Dihydro-1-(2,4,6-triisopropylphenylsulfonyl) benz[cd]indol-5(1H)-one

To a solution of 1-(2,4,6-triisopropylphenylsulfonyl)-indole-3-propionic acid (76.22 g) in chloroform (500 ml) was added dropwise thionyl chloride (28.9 ml) at room temperature taking about 10 minutes. The mixture was stirred for one hour at 60° C. After completion of the reaction, the solvent was distilled off under reduced pressure. To the residue was again added chloroform, followed by concentration under reduced pressure. The concentrate was dissolved in dichloroethane (900 ml). To the solution was gradually added, under ice-cooling, crushed aluminum chloride (58.4 g). The mixture was stirred for 30 minutes, and was added to a mixture of 1N hydrochloric acid (1000 ml) and ice (200 g), followed by extraction with chloroform (900 ml). The extract solution was washed with water (900 ml), dried over anhydrous magnesium sulfate, and was concentrated under reduced pressure. The concentrate was purified by means of a column chromatography (eluted with ethyl acetate:n-hexane=1:4), followed by recrystallization from ethyl acetate-hexane to afford the title compound (43.86 g, m.p.124°–130° C.).

$^1$H-NMR(CDCl$_3$, 200 MHz) δ: 1.10(d,J=7 Hz,12H), 1.25(d,J=7 Hz,6H), 2.87(t,J=7 Hz,2H), 3.21(t,J=7 Hz,2H), 4.18(hep,J=7 Hz,1H), 7.2–7.4(m,4H), 7.68(d,J=9 Hz,2H) ppm.

Reference Example 11

4-Azido-3,4-dihydro-1-(2,4,6-triisopropylphenylsulfonyl)benz[cd]indo-5(1H)-one

To a solution of 3,4-dihydro-1-(2,4,6-triisopropylphenylsulfonyl)benz[cd]indol-5 (1H)-one (5.1 g, 14.3 mmol.) in THF (60 ml) was gradually added under stirring at −45° C. a solution of Me$_3$PhBr$_3$ (5.38 g, 14.3 mmol.) in THF (20 ml) to raise the temperature of the reaction system up to 10° C. After completion of the reaction, insolubles were filtered off, and the filtrate was subjected to distillation under reduced pressure to leave 7.5 g (100%) of 3,4-dihydro-4-bromo-1-(2,4,6-triisopropylphenylsulfonyl)benz[cd]indol-5(1H)-one as a crude crystalline product. Then, this crude crystalline product was dissolved in a mixture of N,N-dimethylformamide (140 ml) and acetic acid (2 ml). To the solution was gradually added, while stirring at −28° C., an aqueous solution (14 ml) of sodium azide (1.86 g, 28.6 mmol.) to raise the temperature of the reaction system up to near 0° C. After completion of the reaction, the reaction mixture was added to ice-water (300 ml). Crystals then precipitated were collected by filtration and dissolved in ethyl acetate. The solution was shaken to allow two layers to be formed. The organic layer was washed with an aqueous saline solution, and was then dried (anhydrous Na$_2$SO$_4$). The solvent was distilled off under reduced pressure to leave 5.67 g (100%) of the title compound as a crude crystalline product. A portion of the product was recrystallized from ethyl acetate to give a product, m.p.129°–132° C.

$^1$H-NMR(CDCl$_3$, 200 MHz) δ: 1.12(d,J=7 Hz,12H), 1.28(d,J=7 Hz,6H), 2.94(t,J=7 Hz,1H), 3.16(ddd,J=16,11,2 Hz,1H), 3.48(dd,J=16,7 Hz,1H), 4.18(hep,J=7 Hz,2H), 4.49(dd,J=11,7 Hz,1H), 7.21(s,2H), 7.31(s,1H), 7.40(t,J=8 Hz,1H), 7.76(d,J=8 Hz,1H×2) ppm. IR(KBr): 2970, 2110, 1695, 1600 cm$^{-1}$. Anal: Calcd for C$_{26}$H$_{30}$N$_4$O$_3$S·0.5H$_2$O; C 64.04%, H 6.41%, N 11.49% Found; C 64.55%, H 6.27%, N 11.20%.

Reference Example 12

4-Acetylamino-3,4-dihydro-1-(2,4,6-triisopropylphenylsulfonyl)benz[cd]indol-5(1H)-one A solution of 4-azido-3,4-dihydro-1-(2,4,6-triisopropylphenylsulfonyl)benz[cd]indol-5(1H)-one (5.36 g, 11.2 mmol), acetic anhydride (2.29 g, 22.4 mmol) and 10% Pd-C (1.7 g in THF (60 ml) was stirred for 4 hours at 4 hours under 4 atmospheres pressure under hydrogen atmosphere. After completion of the reaction, the catalyst was filtered off. The filtrate was concentrated under reduced pressure. To the concentrate was added isopropyl ether to give 5.03 g (91%) of the title compound.

m.p.: 159°–162° C. $^1$H-NMR(CDCl$_3$, 200 MHz) δ: 1.07, 1.10, 1.26(d,J=7 Hz, 6H×3), 2.13(s,3H), 2.85(ddd, J=15, 12, 2 Hz, 1H), 2.92*hep, J=7 Hz, 1H), 3.95(dd, J=15, 7 Hz, 1H), 4.16(hep, J=7 Hz, 2H), 4.85(ddd, J=12, 7, 6 Hz, 1H), 6.71(d, J=6 Hz, 1H), 7.19(s, 2H), 7.23(d, J=2 Hz, 1H), 7.38(t, J=8 Hz), 1H), 7.68, 7.76(d, J=8 Hz, 1H) ppm. IR(KBr); 3420, 3380, 2960, 1690, 1875, 1600 cm$^{-1}$. Anal: Calcd. for C$_{28}$H$_{34}$N$_2$O$_4$ C 67.99%, H 6.93%, N 5.66% Found; C 67.72%, H 7.07%, N 5.59%.

Reference Example 13

4-Trifluoroacetyl-3,4-dihydro-1-(2,4,6-triisopropylphenylsulfonyl)benz[cd]indol-5(1H)-one In 100 ml of ethanol was suspended 1.00 g (2.09 mmol) of 4-azido-3,4-dihydro-1-(2,4,6-triisopropylphenylsulfonyl)benz[cd]indol-5(1H)-one, to which was added 1.0 ml of conc. HCl. The mixture was warmed to make a solution, to which was added 0.10 g of 10% Pd-C (hydrous), followed by hydrogenation for one hour at room temperature. The reaction mixture was subjected to filtration to remove the catalyst. The filtrate was washed with ethanol and concentrated under reduced pressure. To the concentrate was added ether, and the mixture was concentrated twice, followed by crystallization from ether. The crystalline product was collected by filtration, washed with ether and dried under reduced pressure to afford 0.87 g of a 4-amino derivative. The yield was 85%.

0.40 g (0.818 mmol) of the 4-amino derivative obtained as above was dissolved in 6 ml of methylene chloride. To the solution was added, under ice-cooling, 0.14 ml (1.2 equivalent) of anhydrous trifluoroacetic acid and 0.27 ml of triethylamine. The mixture was stirred for 15 minutes, and was then concentrated under reduced pressure. To the concentrate were added ethyl acetate and 1N HCl, and the mixture was shaken to allow two layers to be formed. The organic layer was dried over anhydrous magnesium sulfate, and was concentrated under reduced pressure. The concentrate was purified by means of a silica gel column chromatography (elution with hexane ethyl acetate 9:1). Fractions were combined and concentrated, and there was added a small volume of hexane to cause crystallization. The crystalline product was dried under reduced pressure to afford 0.23 g of the title compound. The yield was 51%.

m.p. :155°– 156° C. $^1$H-NMR(CDCl$_3$, 200 MHz) δ: 1.09, 1.12, 1.26(d, J=7 Hz, 6H×3), 2.93(hep, J=7 Hz, 1H), 2.96(ddd, 15, 12, 2 Hz, 1H), 4.04(dd, J=15, 7 Hz, 1H), 4.15(hep, J=7 Hz, 2H), 4.83(ddd, J=12, 7, 6 Hz, 1H), 7.21(s,2H), 7.29(d,J=2 Hz, 1H), 7.41(t,J=8 Hz, 1H), 7.67(d, J=6 Hz, 1H), 7.73, 7.8(d,J=8 Hz, 1H) ppm. IR(KBr): 2950, 1730, 1685, 1600 cm$^{-1}$. Anal: calcd for C$_{28}$H$_{31}$F$_3$N$_2$O$_4$S; C 61.30% H 5.70%, N 5.11% Found; C 61.24%, H 5.80%, N 4.95%. solution of 1M vinyl magnesium bromide in THF (8 equivalents relative ketone compound) at −40° C. in argon streams. The mixture was warmed up to room temperature, and was stirred for 4 hours at the same temperature range. The reaction mixture was added to an ice-cooled saturated aqueous solution of NH$_4$Cl. The mixture was subjected to extraction with ethyl acetate. The extract was washed with an aqueous saline solution and dried (anhydrous Na$_2$SO$_4$). The solvent was distilled off under reduced pressure. The residue was subjected to a silica gel column chromatography, eluting with n-hexane-ethyl acetate (1:2) to give 0.75 g (24%) of the title compound as an amorphous crystalline product.

$^1$H-NMR(CDCl$_3$, 200 MHz) δ: 1.08(d,J=7 Hz,12H), 1.24(d, J=7 Hz,6H), 2.00(s,3H), 2.6–3.0(m,2H), 3.18(dd,J= 16,5 Hz,1H), 4.15(hep,J=7 Hz,2H), 4.51(dt,J=7, 4 Hz, 1H), 5.31(dd,J=17, 10 Hz, 1H), 5.50(d,J=10 Hz,1H), 5.73(dd,J=17, 10 Hz,1H), 7.1–7.4(m,6H) ppm. IR(KBr): 3390, 2960, 1657 cm$^{-1}$. Anal: Calcd for $C_{30}H_{38}N_2O_4S.H_2O$; C 66.64%, H 7.4%, N 5.18% Found; C 66.35%, H 7.2%, N 4.7%.

Example 1-2

3,4-Dihydro-4-ethylamino-5-hydroxy-1-(2,4,6-triisopropylphenylsulfonyl)-5-vinyl-5H-benz[cd]indole LAH (5 equivalents) was allowed to react with a THF solution (14.3 ml) of 4-acetylamino-3,4-dihydro-5-hydroxy-1-(2,4,6-triisopropylphenylsulfonyl)-5-vinyl-5H-benz[cd]indole (750 mg, 1.43 mmol) and was refluxed for 3 hours to complete the reaction. Ethanol was added to the reaction mixture to inactivate the excess amount of LAH and was added aqueous solution of $Na_2SO_4$. The reaction mixture was subjected to extraction with ethyl acetate. The extract was washed with an aqueous saline solution and, then, dried (anhydrous $Na_2SO_4$) and concentrated under reduced pressure. The residue thus obtained was subjected to silica gel column chromatography, eluting with ethyl acetate to afford 275 mg (38%) of the title compound as an oily product.

$^1$H-NMR(CDCl$_3$, 200 MHz) δ: 1.11, 1.12(d,J=7 Hz, 6H×2), 1.25(d,J=7 Hz,6H), 2.4–3.1(m,5H), 3.30(dd,J=15,4 Hz,1H), 4.18(hept,J=7 Hz,2H), 5.0–5.3(m,2H), 5.92(dd,J=17,11 Hz,1H), 7.1–7.4(m,6H) ppm.

Example 1-3

Trans-4,6,6a,7,9,10a-hexahydro-7-ethyl-4-(2,4,6-triisopropylphenylsulfonyl)-10a-vinyl-indolo[3,4-gh][1.4]benzoxazin-8-one To a solution of 3,4-dihydro-4-ethylamino-5-hydroxy-1-(2,4,6-triisopropylphenylsulfonyl)-5-vinyl5H-benz[cd]indole (270 mg, 0.53 mmol) in ethyl acetate (5.3 ml) was added a saturated aqueous solution of sodium carbonate (5.3 ml). To the mixture was added, while vigorously stirring, chloroacetyl chloride (1.2 equivalent). After completion of the reaction, the organic layer was separated and washed with an aqueous saline solution, followed by drying (anhydrous $Na_2SO_4$). The solvent was distilled off under reduced pressure to leave the residue (260 mg). To a solution of the chloroacetyl compound in THF-acetonitrile (5:1, 5ml) was added, while stirring under ice-cooling, 60% sodium hydride (2 equivalents), and the mixture was stirred for 2–3 hours at room temperature. After completion of the reaction, the reaction mixture was added to a saturated aqueous solution of $NH_4Cl$ cooled with ice, followed by extraction with ethyl acetate. The extract solution was dried (anhydrous $Na_2SO_4$), then the solvent was distilled off. The residue was subjected to silica gel column chromatography, eluting with n-hexane-ethyl acetate (3:1) to afford 208 mg (86%) of the title compound as an amorphous crystalline product.

$^1$H-NMR(CDCl$_3$, 200MHz) δ: 1.07(d,J=7 Hz,12H), 1.24(d,J=7 Hz,6H), 2.7–3.0(m,2H), 3.35(m,2H), 3.9–4.2(m, 4H), 4.40, 4.48 (d,J=17 Hz, 1H×2), 4.91(d,J=18 Hz, 1H), 5.36(d,J=11 Hz,1H), 6.24(dd,J=18,11 Hz,1H), 7.1– 7.4(m, 6H) ppm. IR(KBr): 2962, 1662 cm$^{-1}$. Anal: Calcd for $C_{32}H_{40}N_2O_4S.0.5H_2O$; C 68.91%, H 7878 .41%, N 5.02% Found; C 68.86%, H 7.45%, N 4.69%.

Example 1-4

Trans-4,6,6a,8,9,10a-hexahydro-7-ethyl 1-4-(2,4,6-triisopropylphenylsulfonyl)-10a-vinyl-7H-indolo[3,4-gh][1.4]benzoxazine To a solution of trans-4,6,6a,7,9,10a-hexahydro-7-ethyl-4-(2,4,6-triisopropylphenylsulfonyl)- 10a-vinyl-indolo[3,4-gh][1.4]benzoxazin-8-one (200 mg, 0.36 mmol) in THF (3.6 ml) was added LAH (3 equivalents) while stirring under ice-cooling, and the mixture was heated for 3 hours under reflux. After completion of the reaction, ethanol was added to the reaction mixture to inactivate the excess amount of LAH, followed by addition to an ice-cooled saturated aqueous solution of $Na_2SO_4$. The mixture was subjected to extraction with ethyl acetate. The extract solution was washed with an aqueous saline solution and, then, dried (anhydrous $Na_2SO_4$). The solvent was distilled off under reduced pressure, and the residue was subjected to silica gel column chromatography, eluting with n-hexane-ethyl acetate (17:3) to afford 103 mg (54%) of the title compound as an amorphous crystalline product.

$^1$H-NMR(CDCl$_3$, 200MHz) δ: 1.06, 1.07 (d,J=7 Hz, 6H×2), 1.23(d,J=7 Hz,6H), 2.5–3.0(m,7H), 3.21(dd,J=15, 4 Hz,1H), 3.80(dd,J=11, 3 Hz,1H), 4.1–4.4(m,3H), 4.76(dd, J=18, 2 Hz,1H), 5.23(dd,J=11, 2 Hz,1H), 6.62(dd,J=18, 11 Hz,1H), 7.1–7.3(m,6H) ppm. IR(KBr): 2975 cm$^{-1}$. Anal: Calcd. for $C_{32}H_{42}N_2O_3S.0.5H_2O$; C 70.68%, H 7.97%, N 5.15% Found; C 71.07%, H 7.85%, N 5.48%.

Example 1-5

Trans-4,6,6a,8,9,10a-hexahydro-7-ethyl-10a-vinyl-7H-indolo[3,4-gh][1.4]benzoxazine To a solution of trans-4,6,6a,8,9,10a-hexahydro-7-ethyl 1-4-(2,4,6-triisopropylphenylsulfonyl)-10a-vinyl-7H-indolo [3,4-gh][1.4]benzoxazine ( 100 mg, 0.18 mmol) in THF (5.4 ml) was added, at room temperature, a solution of 0.5M naphthalene sodium in THF (10 equivalents) in argon streams. The mixture was stirred for 10 minutes at room temperature, and was then added to an ice-cooled saturated aqueous solution of $NH_4Cl$, followed by extraction with ethyl acetate. The organic layer was washed with an aqueous saline solution and dried ($Na_2SO_4$). The solvent was distilled off under reduced pressure, and the residue was subjected to a silica gel column chromatography, eluting with n-hexane-ethyl acetate (1:1) to afford 33 mg (68%) of the title compound as an amorphous crystalline product.

$^1$H-NMR(CDCl$_3$, 200MHz) δ: 1.05(t,J=7 Hz,3H), 2.6–3.1(m,6H), 3.31(dd,J=15, 4 Hz,1H), 3.83(ddd,J=11.4, 1 Hz,1H), 4.32(dt,J=11, 3 Hz,1H), 5.00(dd,J=17, 2 Hz,1H), 5.27(dd,J=11, 2 Hz,1H), 6.59(dd,J=17, 11 Hz,1H), 6.88(t, J=2 Hz,1H), 7.1–7.3(m,3H), 7.8–8.0(br,1H) ppm. IR(KBr): 3410, 2960 cm$^{-1}$. Anal: Calcd for $C_{17}H_{20}N_2O.0.9H_2O$; C 71.75%, H 7.72%, N 9.84% Found; C 71.68%, H 7.25%, N 9.58%.

Example 2-1

4-Acetylamino-3,4-dihydro-5-hydroxy-5-methyl-1-(2,4,6- triisopropylphenylsulfonyl)-5H-benz[cd]indole To a solution of 4-acetylamino-3,4-dihydro-1-(2,4,6-triisopropylphenylsulfonyl)-benz[cd]indol-5-one (3.57 g, 7.0 mmol) in THF (70 ml) was added, at 40° C. in argon streams, a solution of 1M methyl magnesium bromide in THF (8 equivalents relative to ketone compound). The mixture was warmed to room temperature, and stirred for 4 hours. The reaction mixture was added to an ice-cooled saturated aqueous solution of $NH_4Cl$ and the mixture was subjected to extraction with ethyl acetate. The extract was washed with an aqueous saline solution and, then, dried (anhydrous $Na_2SO_4$). The solvent was distilled off under reduced pressure. The residue was subjected to a silica gel column chromatography, eluting with n-hexane-ethyl acetate (1:2) to afford 1.27 g (36%) of the title compound as an amorphous crystalline product. $^1$H-NMR(CDCl$_3$, 200MHz) δ: 1.09(d, J=7 Hz,12H), 1.25(d,J=7 Hz,6H), 1.95(s,3H), 2.7–3.0(m, 2H), 3.24(dd,J=16, 5 Hz,1H), 4.14(hept,J=7 Hz,2H), 4.54(m,1H), 5.3–5.5(br,1H), 7.1–7.4(m,6H) ppm. IR(KBr):3390, 2965, 1660 cm$^{-1}$. Anal: Calcd for C$_{29}$H$_{38}$N$_2$O$_4$S.H$_2$O: C 65.88%, H 7.63%, N 5.30% Found; C 66.13%, H 7.28%, N 5.69%.

Example 2-2

3,4-Dihydro-4-ethylamino-5-hydroxy-6-methoxy-5-methyl-5H-benz[cd]indole

In substantially the same manner as in Example 1-2, 4-acetylamino-3,4-dihydro-5-hydroxy-6-methoxy- 5-methyl-1-p-toluenesulfonyl-5H-benz[cd]indole (2.0 g, 4.85 mmol) was subjected to reduction. The residue thus obtained was subjected to a silica gel column chromatography, eluting with ethyl acetate-methanol, (20:1) to afford 953 mg (76%) of the title compound as an amorphous crystalline product, m.p.185°–187° C. (decomposed: as fumarate).

$^1$H-NMR(CDCl$_3$, 200 MHz) δ: 1.22(t,J=7 Hz, 3H), 1.53(s,3H), 2.5–2.8(m,2H), 2.98(dq,J=11, 7 Hz,1H), 3.94(s, 3H), 6.8– 7.2(m,3H), 7.96(br s,1H) ppm. Anal: Calcd. for C$_{19}$H$_{24}$N$_2$O$_6$.0.5C$_4$H$_4$O$_4$: C 64.13%, H 6.96%, N 8.80% Found; C 63.77%, H 7.17%, N 8.79% as fumarate

Example 2-3

Trans-4,6,6a,7,9,10a-hexahydro-7-ethyl-1-methoxy-10a-methyl-indolo[3,4-gh][1.4] benzoxazin-8-one To a solution of 3,4-dihydro-4-ethylamino-5-hydroxy-6-methoxy-5-methyl-5H-benz[cd]indole ( 646 mg 2.48 mmol) in ethyl acetate (25 ml) was added a saturated aqueous solution of sodium carbonate (24 ml). To the mixture was added, while stirring vigorously, chloroacetyl chloride (1.2 equivalent). After completion of the reaction, the organic layer was separated and washed with an aqueous saline solution, followed by drying (anhydrous Na$_2$SO$_4$). The solvent was distilled off under reduced pressure. The residue was cyclized and, then, purified by means of silica gel column chromatography (eluting with n-hexane-ethyl acetate (2:7)) to afford 517 mg (72%) of the title compound as an amorphous crystalline product.

$^1$H-NMR(CDCl$_3$, 200 MHz) δ: 1.21(t,d=7 Hz,3H), 1.57(s, 3H), 2.76(ddd,J=14, 13, 2 Hz, 1H), 3.38(m,2H), 3.88(s,3H), 4.0–4.3(m,2H), 4.44, 4.55 (d,J=17 Hz, 1H×2), 6.9– 7.3(m, 3H), 7.94(br s, 1H) ppm. IR(KBr):3348, 2988, 1645 cm$^{-1}$. Anal: Calcd for C$_{17}$H$_{20}$N$_2$O$_3$.1.5H$_2$: C 62.37%, H 7.08%, N 8.56% Found; C 62.04%, H 6.30%, N 8.45%.

Example 2-4

Trans-4,6,6a,8,9,10a-hexahydro-7-ethyl-1-methoxy-10a-methyl-7H-indole[3,4-gh][1.4] benzoxazine Trans-4,6,6a,7,9,10a-hexahydro-7-ethyl-1-methoxy-10a-methyl-indolo[3,4-gh] [1.4]benzoxazin-8-one (500 mg, 1.67 mmol) was subjected to reduction, and the resultant product was recrystallized from chloroform-n-hexane to afford the title compound (320 mg, 67%, m.p.215°–217° C.(dec.)).

$^1$H-NMR(CDCl$_3$, 200 MHz) δ: 1.05(t,d=7 Hz,3H), 1.59(s, 3H), 2.4–3.0(m,6H), 3.24(dd,J=17, 4 Hz, 1H), 3.87(s,3H), 4.22(dt,J=12, 3 Hz,1H), 6.8–7.2(m,3H), 7.78(br s, 1H) ppm.

IR(KBr): 3320, 2959, 2803 cm$^{-1}$. Anal: Calcd for C$_{17}$H$_{22}$N$_2$O$_2$.0.3H$_2$O; C 69.97%, H 7.81%, N 9.60% Found; C 69.99%, H 7.60%, N 9.48%.

Example 3-1

3,4-Dihydro-5-hydroxy-5-methyl-4-trifluoroacetylamino-1-(2,4,6-triisopropylphenylsulfonyl)-5 H-benz[cd]indole Methyl magnesium bromide (1M THF solution 8 equivalents) was allowed to react with a solution of 3,4-dihydro-4-trifluoroacetylamino-1-(2,4,6-triisopropylphenylsulfonyl)-5H-benz[cd]indol-5-one (1.5 g, 1.43 mmol) in THF (14.3 ml). The reaction mixture was processed in a conventional manner. The residue was subjected to silica gel column chromatography, eluting with n-hexane-ethyl acetate (4:1) to afford 1.3 g (84%) of the title compound as an amorphous crystalline product.

$^1$H-NMR(CDCl$_3$, 200MHz) δ: 1.08(d,J=7 Hz,12H), 1.25(d,J=7 Hz,6H), 1.59(s,3H), 2.8–3.0(m,2H), 3.40(dd,J= 18, 6 Hz,1H), 4.15(hept,J=7 Hz,2H), 4.55(m,1H), 6.0–6.2(br,1H), 7.2–7.5(m,6H) ppm. IR(KBr): 3413, 2960, 1720 cm$^{-1}$. Anal: Calcd for C$_{29}$H$_{35}$N$_2$O$_4$SF$_3$.0.5H$_2$; C 60.72%, H 6.33%, N 4.88% Found; C 60.59%, H 6.18%, 4.55%.

Example 3-2

4-Amino-3,4-dihydro-5-hydroxy-5-methyl-1-(2,4,6-triisopropylphenylsulfonyl)-5H-benz[cd]indole To an ethanol solution (9 ml) of 3,4-dihydro-5-hydroxy-5-methyl-4-trifluoroacetyl-1-( 2,4,6-triisopropylphenylsulfonyl)-5H-benz[cd]indole (640 mg, 0.91 mmol) was added 1N sodium hydroxide (2 equivalents). The mixture was heated for one hour under reflux. After completion of the reaction, the reaction mixture was concentrated under reduced pressure. The concentrate was shaken with chloroform-water, and was left standing to form two layers. The organic layer was separated and washed with an aqueous saline solution, followed by drying (anhydrous Na$_2$SO$_4$). The solvent was distilled off under reduced pressure. The residue was subjected to a silica gel column chromatography, eluting with ethyl acetate-methanoltriethylamine (50:5:1) to afford 290 mg (68%) of the title compound as an amorphous crystalline product.

$^1$H-NMR(CDCl$_3$, 200MHz) δ: 1.07(d,J=7 Hz,12H), 1.24(d,J=7 Hz,6H), 1.37(s,3H), 2.89(hep,J=7 Hz,1H), 3.1–3.4(m,2H), 4.15(hep,J=7 Hz,2H), 7.1–7.4(m,2H) ppm. SIMS: MH$^+$=469.

Example 3-3

Trans-4,6,6a,7,9,10a-hexahydro-10a-methyl-1-(2,4,6-triisopropylphenylsulfonyl)-indolo[3,4-gh][1.4]benzoxazin-8-one To a solution of 4-amino-3,4-dihydro-5-hydroxy-5-methyl-1-(2,4,6-triisopropylphenylsulfonyl)- 5H-benz[cd]indole (234 mg, 0.5 mmol) in ethyl acetate (5 ml) was added a saturated aqueous solution of sodium carbonate (5 ml). To the mixture was added, while stirring vigorously, chloroacetyl chloride (1.2 equivalent). After completion of the reaction, the organic layer was separated and washed with an aqueous saline solution, followed by drying (anhydrous Na$_2$SO$_4$). The solvent was distilled off under reduced pressure. The residue was subjected to cyclization substantially in accordance with Example 1-3. The residue thus obtained was subjected to a silica gel column chromatography, eluting with n-hexane-ethyl acetate (1:1) to afford 247 mg (99%) of the title compound as a crude crystalline product. A portion of the crystals was recrystallized (n-hexane-ethyl acetate) to give a pure product (m.p.125–127 deg.)

$^1$H-NMR(CDCl$_3$, 200MHz) δ: 1.07, 1.08 (d,J=7 Hz, 6H×2), 1.24(d,J=7 Hz,6H), 1.45(s,3H), 2.6–3.1(m,3H), 4.00(dd,J=14, 6 Hz,1H), 4.15(hep,J=7 Hz,2H), 4.47(s,2H), 6.48(br s,1H), 7.1–7.4(m,6H) ppm. IR(KBr): 2960, 1684 cm$^{-1}$. SIMS:MH$^+$=509.

Example 3-4

Trans-4,6,6a,8,9,10a-hexahydro-10a-methyl-1-(2,4,6-triisopropylphenylsulfonyl)-7H-indolo[3,4-gh][1.4]benzoxazine To a solution of trans-4,6,6a,7,9,10a-hexahydro-10a-methyl-1-(2,4,6-triisopropylphenylsulfonyl)-indolo[3,4-gh][1.4]benzoxazin-8-one (220 mg, 0.43 mmol) in THF (10 ml) was added, while stirring under ice-cooling, LAH (3 equivalents). The mixture was heated for 3 hours under reflux. After completion of the reaction, ethanol was added to the reaction mixture to inactivate the excess amount of LAH. The reaction mixture was added to an ice-cooled saturated aqueous solution of Na$_2$SO$_4$, followed by extraction with ethyl acetate. The extract solution was washed with an aqueous saline solution, followed by drying (anhydrous Na$_2$SO$_4$). The solvent was distilled off under reduced pressure. The residue was subjected to a silica gel column chromatography, eluting with n-hexane-ethyl acetate (1:5), to afford 106 mg (50%) of the title compound as a syrupy product.

$^1$H-NMR(CDCl$_3$, 200 MHz) δ: 1.07(d,J=7 Hz,12H), 1.23(d,J=7 Hz,6H), 1.44(s,3H), 2.58(ddd,J=14, 12, 2 Hz, 1H), 2.7–3.2(m,5H), 3.79(dd,J=12, 3 Hz,1H), 4.0– 4.3(m, 3H), 7.1–7.3(m,6H) ppm.

Example 3-5

Trans-4,6,6a,8,9,10a-hexahydro-10a-methyl-7H-indolo[3,4-gh][1.4]benzoxazine

Lithium aluminum hydride (5 equivalents) was allowed to react with a THF solution (20 ml) of trans-4,6,6a,8,9,10a-hexahydro-10a-methyl-1-( 2,4,6-triisopropylphenylsulfonyl)-7H-indolo[3,4-gh][1.4]benzoxazin-8-one (1.2 g, 2.36 mmol). The residue thus obtained was subjected to a silica gel column chromatography, eluting with ethyl acetate, to afford 100 mg (15%) of the title compound.

$^1$H-NMR(CDCl$_3$, 200MHz) δ: 1.51(s,3H), 2.66(ddd,J= 15, 12, 2 Hz, 1H), 2.8–3.3(m,4H), 3.82(dd, J=11, 3 Hz, 1H), 4.13(dt,J=12, 3 Hz, 1H), 6.87(br s, 1H), 7.1–7.2(m,3H), 8.0–b 8.1(br,1H) ppm. IR(KBr): 3410, 2935 cm$^{-1}$. Anal: Calcd for C$_{14}$H$_{16}$N$_2$O.1.0H$_2$O; C 68.27%, H 7.37%, N 11.37% Found; C 68.12%, H 7.01%, N 11.10%.

Example 4

4,6,6a,8,9,10a-Hexahydro-10a-methyl-7-(4-phthalimidobutyl)-7H-indolo[3,4-gh][1.4]benzoxazine To a solution of 4,6,6a,8,9,10a-hexahydro-10a-methylindolo[ 3,4-gh][1.4]benzoxazine (100 mg, 0.44 mmol) in DMF (5 ml) were added potassium carbonate (303 mg, 2.2 mmol), N-(4=bromobutyl)phthalimido (124 mg, 0.44 mmol) and sodium iodide (0.66 mg, 0.44 mmol). The mixture was heated at 60° C. for 24 hours. After completion of the reaction, the reaction mixture was added to ice water-ethyl acetate. The organic layer was separated, washed with a saturated aqueous saline solution and dried over anhydrous sodium sulfate. The solvent was distilled off under reduced pressure. The residue was subjected to a silica gel column chromatography, eluting with n-hexane-ethyl acetate (3:2), to afford 130 mg (69%) of the title compound as an amorphous crystalline product.

$^1$H-NMR(CDCl$_3$, 200 MHz) δ: 1.52(s,3H), 1.5–1.9(m, 4H), 2.3–3.0(m,6H), 3.28(dd,J=14, 4 Hz,1H), 3.75(t,J=7 Hz,2H), 4.18(dt,J=12, 3 Hz,1H), 6.90(br s, 1H), 7.1–7.2(m, 3H), 7.7–7.8 (m, 2H), 7.8–7.9(m,2H), 7.96(br s, 1H) ppm. IR (KBr): 3411, 2945, 1710 cm$^{-1}$. Anal: Calcd for C$_{26}$H$_{27}$N$_3$O$_3$.1.0H$_2$O; C 69.78%, N 9.39% Found; C 69.61%, H 6.18%, N 8.90%.

Example 5

4,6,6a,8,9,10a-Hexahydro-10a-methyl-7-(2-phenoxyethyl)-7H-indolo[3,4-gh][1.4]benzoxazine To a solution of 4,6,6a,8,9,10a-hexahydro-10a-methyl-7H-indolo[3,4-gh][1.4]benzoxazine (85 mg, 0.37 mmol) in DMF (5 ml) were added potassium carbonate (255 mg, 1.9 mmol) and 1-iodo-2-phenoxyethane (99 mg, 0.4 mmol). The mixture was heated at 60° C for 24 hours. After completion of the reaction, the reaction mixture was added to a mixture of ice water and ethyl acetate. The organic layer was separated, washed with a saturated aqueous saline solution and dried over anhydrous sodium sulfate. The solvent was distilled off under reduced pressure, and the residue was subjected to a silica gel column chromatography, eluting with n-hexane-ethyl acetate (2:1), to afford 59 mg (46%) of the title compound as an amorphous crystalline product.

$^1$H-NMR(CDCl$_3$, 200MHz) δ: 1.54(s,3H), 2.5–3.0(m, 5H), 3.2–3.4(m,2H), 3.82(dd,J=12,3 Hz,1H), 4.1–4.3(m, 3H), 6.9–7.9(m,9H), 7.95(br s,1H) ppm. IR(KBr): 3412, 2947, 1710 cm$^{-1}$. Anal: Calcd for C$_{22}$H$_{24}$N$_2$O$_2$.0.5H$_2$O; C 73.92%, H 7.05%, N 7.84% Found; C 73.44%, H 6.82%, N 7.10%.

Example 6-1

Trans-7-chloroacetyl-4,6,6a,8,9,10a-hexahydro-10a-methyl-1-(2,4,6-triisopropylphenylsulfonyl)-7 H-indolo[3,4-gh][1.4]benzoxazine To a solution of trans-4,6,6a,8,9,10a-hexahydro-10a-methyl- 1-(2,4,6-triisopropylphenylsulfonyl)-7H-indolo[3,4-gh][1.4]benzoxazine (106 mg, 0.21 mmol) in ethyl acetate (10 ml) was added a saturated aqueous solution of sodium carbonate (2 ml). To the mixture was added, while stirring vigorously, chloroacetyl chloride (1.2 equivalent). After completion of the reaction, the organic layer was separated, washed with an aqueous saline solution and dried (anhydrous Na$_2$SO$_4$). The solvent was distilled off under reduced pressure, and the residue was subjected to a silica gel column chromatography, eluting with n-hexane-ethyl acetate (4:1) to afford 109 mg (89%) of the title compound as an amorphous crystalline product.

$^{-1}$H-NMR(CDCl$_3$, 200MHz) δ: 1.08, 1.085(d,J=7 Hz, 6H×2), 1.24(d,J=7 Hz,6H), 2.89(hep,J=7 Hz,1H), 3.45(dd, J=17, 4 Hz,1H), 3.68(dd,J=12, 4 Hz,1H), 3.8–4.2(m,7H), 7.1–7.4(m,6H) ppm. IR(KBr): 2965, 1668 cm$^{-1}$. Anal: Calcd for C$_{31}$H$_{39}$N$_2$O$_4$SCl; C 65.19%, H 6.88%, N 4.90%

Found; C 64.78%, H 6.84%, N 4.82%.

Example 6-2

Trans-7-[2-(4-benzylpiperazin-1-yl)-1-oxoethyl]-4,6,6a,8,9,10a-hexahydro-10a-methyl-4-(2,4,6-triisopropylphenylsulfonyl)-7H-indolo[3,4-gh][1.4]benzoxazine To a solution of trans-7-chloroacetyl-4,6,6a,8,9,10a-hexahydro-10a-methyl-1-(2,4,6 -triisopropylphenylsulfonyl)-7H-indolo[3,4-gh][1.4]benzoxazine (77 mg, 0.14 mmol) in DMF (2.5 ml) were added potassium carbonate (82 mg, 0.6 mmol) and benzyl piperazine (0.025 ml, 0.14 ml). The mixture was stirred for 8 hours at room temperature. After completion of the reaction, a mixture of ice-water and ethyl acetate was added the reaction mixture. The organic layer was separated, washed with a saturated aqueous saline solution and dried over anhydrous sodium sulfate. Under reduced pressure, the solvent was distilled off to leave 81 mg (85%) of the title compound as a crystalline product. A portion of the crystals was recrystallized from ether-n-hexane (m.p.82–84 deg.)

$^1$H-NMR(CDCl$_3$, 200 MHz) δ: 1.07, 1.08 (d,J=7 Hz, 6H×2), 1.23(d,J=7 Hz,6H), 1.50(s,3H), 2.3–2.7(m,8H), 3.10, 3.29 (d,J=14 Hz, 1H×2), 3.52(s,2H), 3.61(dd, J=12, 4 Hz, 1H), 3.8–4.2(m,3H), 7.1–7.4(m, 11H) ppm. IR(KBr): 2960, 1652 cm$^{-1}$. Anal: Calcd for C$_{42}$H$_{54}$ N$_4$O$_4$.2.0H$_2$O; C 67.53%, H 7.83%, N 7.50% Found; C 67.47%, H 7.31%, N 7.27%.

Example 6-3

Trans-7-[2-(4-benzylpiperazin-1-yl)-ethyl]-4,6,6a,8,9,10a-hexahydro-10a-methyl-7H-indolo[3,4-gh]1,4]benzoxazine 7-[2-(4-benzylpiperazin-1-yl)-1-oxoethyl]- 4,6,6a,8,9,10a-hexahydro-10a-methyl-4-(2,4,6-triisopropylphenylsulfonyl)-7H-indro[3,4-gh][1.4]benzoxazine (71 mg, 0.1 mmole) was subjected to LAH reduction. The compound thus reduced was subjected to silica gel column chromatography, eluting with ethyl acetate-methanol (20:1), to afford 29 mg (67%) of the title compound as an amorphous crystalline product.

$^1$H-NMR(CDCl$_3$, 20 MHz) δ: 1.51(s,3H), 2.4–3.1(m, 16H), 3.30 (dd,J=14, 4 Hz, 1H), 3.52(s,2H), 3.81(dd,J=12, 3 Hz,1H), 4.18(dt,J=12, 3 Hz,1H), 6.88(br s, 1H), 7.1– 7.4(m, 8H), 7.97(br s, 1H) ppm. IR(KBr): 3420, 2940, 2810 cm$^{-1}$. Anal: Calcd for C$_{27}$H$_{34}$N$_4$O.2.0H$_2$O; C 69.50%, H 8.21%, N 12.0% Found; C 69.46%, H 7.53%, N 11.8%

Example 7-1

4-Acetylamino-3,4-dihydro-5-hydroxy-6-methoxy-5-phenyl-1-p-toluenesulfonyl-5H-benz[cd]indole In substantially the same manner as Example 1-1, phenyl magnesium bromide (2M THF solution) was allowed to react with 4-acetylamino-3,4-dihydro-6-methoxy-1-p-toluenesulfonylbenz[cd]indol(1H)-5-one (2.0 g, 4.85 mmol). The residue thus obtained was subjected to silica gel column chromatography, eluting with ethyl acetate, to afford 1.1 g (46.2%) of the title compound as an amorphous crystalline product.

$^1$H-NMR(CDCl$_3$, 200MHz) δ: 1.93(s,3H), 2.35(ddd,J= 16, 13, 2 Hz, 1H), 2.38(s,3H), 2.98(dd,J=15, 5 Hz,1H), 3.71(s,3H), 4.72(m,1H), 4.94(s,1H), 5.14(d,J=10 Hz,1H), 6.92(d,J=9 Hz,1H), 7.1–7.9(m,11H) ppm. IR(KBr): 3510, 3424, 1661 cm$^{-1}$. Anal: Calcd for C$_{27}$H$_{26}$N$_2$O$_5$S; C 66.10%, H 5.3%, N 5.71% Found; C 65.93%, H 5.60%, N 5.61%.

Example 7-2

Trans-7-ethyl-4,6,6a,7,9,10a-hexahydro-1-methoxy-10a-phenyl-indolo[3,4-gh][1.4] benzoxazin-8-one 4-Acetylamino 3,4-dihydro-5-hydroxy-6-methoxy-1-p-toluenesulfonyl-5H-benz[cd]indole (600 mg, 1.86 mmol) was cyclized by processing with chloroacetyl chloride according to the method of Example 2-3 to give crude crystals (692 mg). A portion of the crystals was recrystallized (chloroform-n-hexane) to afford a pure product (m.p 278–280 dec.).

$^1$H-NMR(CDCL$_3$, 200 MHz) δ: 0.81(t,J=7 Hz,3H), 3.69(s,3H), 6.95(d,J=9 Hz,1H), 7.2–7.4(m,7H), 8.00(br s, 1H) ppm. IR(KBr): 1655 cm$^{-1}$.

Example 7-3

Trans-7-ethyl-1-methoxy-10a-phenyl-4,6,6a,10a-tetrahydro-7H-indolo[3,4-gh][1.4] benzoxazine Trans-7-ethyl-4,6,6a,8,9,10a-hexahydro-1-methoxy-10a-phenyl-7H-indolo[3,4-gh][1.4] benzoxazin-8-one (664 mg, 1.83 mmol) was reduced with LAH. The residue thus obtained was subjected to a silica gel column chromatography, eluting with n-hexane-ethyl acetate (3:1), to afford 74 mg (12%) of the title compound as a crude crystalline product (m.p.194–196 dec.)

$^1$H-NMR (CDCl$_3$, 200MHz ) δ: 0.97(t,J=7 Hz,3H), 2.7–3.1(m,3H), 3.92(dd,J=15, 5 Hz,1H), 3.61(s,3H), 3.70(dd,J= 13, 5 Hz, 1H), 5.42, 6.37(d,J=5 Hz, 1H×2), 6.88(d,J=9 Hz,1H), 7.02(br s, 1H), 7.1–7.4(m,7H), 7.91(br s, 1H) ppm. IR(KBr): 3355, 2967 cm$^{-1}$, Anal: Calcd for C$_{22}$H$_{22}$N$_2$O$_2$.0.5H$_2$O; C 74.3%, H 6.52%, N 7.88% Found; C 73.91%, H 6.20%, N 7.73%

Example 8-1

Trans-4-acetylamino-3,4-dihydro-5-hydroxy-5-methyl-1-(2,4,6-triisopropylphenylsulfonyl)-5(1H)benz[cd]indole To a solution of 4-acetylamino-3,4-dihydro-1-(2,4,6-triisopropylphenylsulfonyl)-benz[cd]indol-5 (1H)-one (6.0 g, 12.1 mmol) in THF (100 ml) was added at −40° C. in argon streams, a THF solution (97 ml) of 1M methyl magnesium bromide. The mixture was warmed to room temperature and stirred for 4 hours at the same temperature range, and the mixture was added to an ice-cooled saturated aqueous solution of ammonium chloride. The mixture was subjected to extraction with ethyl acetate. The extract was washed with a saturated aqueous saline solution, and was dried (anhydrous sodium sulfate). The solvent was distilled off under reduced pressure. The residue was subjected to a silica gel column chromatography, eluting with n-hexane-ethyl acetate (1:5) to afford 3.6 g (58%) of the title compound as amorphous crystals.

$^1$H-NMR(CDCl$_3$, 200 MHz) δ: 1.09(d,J=7 Hz,12H), 1.25(d,J=7 Hz,6H), 1.95(s,3H), 2.70–3.00(m,2H), 3.24(dd, J=16,5 Hz,1H), 4.14(hept,J=7 Hz,2H), 4.54(m, 1H), 5.30– 5.50(br,1H), 7.10–7.40(m,6H) ppm. IR(KBr): 3390, 2965, 1660 cm$^{-1}$. Anal: Calcd for C$_{29}$H$_{38}$N$_2$O$_4$S.H$_2$O; C 65.88%, H 7.63%, N 5.30% Found; C 66.13%, H 7.28%, N 5.69%.

Example 8-2

Trans-3,4-dihydro-4-ethylamino-5-hydroxy-5-methyl-1-2,4,6-triisopropylphenylsulfonyl)-5 (1H)-benz[cd]indole To a solution of trans-4-acetylamino-3,4-dihydro-5-hydroxy-5-methyl-1-(2,4,6 -triisopropylphenylsulfonyl)-5(1H)-benz[cd] indole in THF (50 ml) was added LAH (5 equivalents). The mixture was heated for 2 hours under reflux. After completion of the reaction, ethanol was added to the reaction mixture to inactivate excess LAH, and the mixture was then added to an ice-cooled saturated aqueous solution of sodium sulfate. The mixture was subjected to extraction with ethyl acetate, and the extract was washed with a saturated aqueous saline solution, followed by drying (anhydrous sodium sulfate). The solvent was distilled off under reduced pressure. The residue was subjected to a silica gel column chromatography, eluting with ethyl acetate to afford 3.05 g (90%) of the title compound as an oily product.

$^1$H-NMR(CDCl$_3$, 200 MHz) δ: 1.07, 1.08(d,J=7 Hz,6H× 2), 1.15(t,J=7 Hz,3H), 1.24(d,J=7 Hz,6H), 2.35–3.10(m, 5H), 3.30(dd,J=15,4 Hz,1H), 4.15(hept,J=7 Hz,2H), 7.10–7.35(m,6H) ppm.

Example 8-3

Trans-4,6,6a,8,9,10a-hexahydro-7-ethyl-10a-methyl-7H-indolo[3,4-gh][1,4]benzoxazine To a solution of trans-3,4-dihydro-4-ethylamino-5-hydroxy-5-methyl-1-(2,4,6 -triisopropylphenylsulfonyl)-5(1H)-benz[cd]indole (3.0 g, 6.0 mmol) in ethyl acetate (60 ml) was added a saturated aqueous solution of sodium carbonate (60 ml). To the solution was added, while vigorously stirring, chloroacetyl chloride (1.2 equivalent). After completion of the reaction, the organic layer was washed with an aqueous saline solution, followed by drying (anhydrous sodium sulfate). The solvent was distilled off under reduced pressure to leave a residue (3.4 g). To a solution of this chloroacetyl compound in THF-DMF (5:3, 80 ml) was added, while stirring under ice-cooling, 60% sodium hydride (2 equivalents). The mixture was stirred for one hour at room temperature. After completion of the reaction, the reaction mixture was added to an ice-cooled saturated aqueous solution of ammonium chloride. The mixture was subjected to extraction with ethyl acetate. The extract was further dried (anhydrous sodium sulfate), then the solvent was distilled off under reduced pressure to leave a residue (2.8 g). To a solution of the obtained residue in THF (50 ml) was added, at room temperature, LAH (8 equivalents), and the mixture was heated for 12 hours under reflux. After completion of the reaction, ethanol was added to the reaction mixture. The mixture was added to an ice-cooled saturated aqueous solution of sodium sulfate, followed by extraction with ethyl acetate. The extract was washed with an aqueous saline solution and dried (anhydrous sodium sulfate). The solvent was distilled off, and the residue was subjected to a silica gel column chromatography, eluting with n-hexane-ethyl acetate (1:1). The eluate was recrystallized from isopropyl ether-n-hexane to give 600 mg (39%) of the title compound, m.p.129°–130° C.

$^1$H-NMR(CDCl$_3$m 200 MHz) δ: 1.04(t,J=7 Hz,3H), 1.53(s,3H), 2.45–3.05(m,6H), 3.28(dd,J=14,4 Hz,1H), 3.84(dd,j=11,3 Hz,1H), 4.21(dt,J=12,3 Hz,1H), 6.88(s,1H) 7.10–7.25(m,3H), 7.85–8.05(br,1H) ppm. IR(KBr): 3275, 2942, 1615, 1602 cm$^{-1}$. Anal: Calcd for C$_{31}$H$_{40}$N$_2$O$_5$; C 74.97%, H 7.86%, N 10.93% Found; C 74.90%, H 7.94%, N 10.92%

Example 9-1

Trans-4,6,6a,7,9,10a-hexahydro-7-methyl-10a-methyl-1-methoxy-4-(2,4,6-triisopropylphenylsulfonyl)-indolo[3,4-gh][1,4]benzoxazin-8-one To a solution of 3,4-dihydro-5-hydroxy-6-methoxy-5-methyl-4-trifluoroacetylamino-1-( 2,4,6- triisopropylphenylsulfonyl)-5H-benz[cd]indole (m.p169°– 171° C., Anal: Calcd. for C$_{29}$H$_{33}$N$_2$O$_5$SF$_3$.0.2H$_2$; C 59.82%, H 5.78% m N 4.81% Found; C 59.59%, H 5.88%, N 4.92%) (3.4 g, 5.7 mmol.), which was synthesized in substantially the same manner as in Reference Example 13, in ethanol (55 ml) was added a 1N aqueous solution of sodium hydroxide (14.3 ml). The mixture was stirred for 30 minutes at 60° C. After completion of the reaction, the solvent was distilled off under reduced pressure. The residue was subjected to extraction with chloroform, and the extract was washed with an aqueous saline solution, followed by drying (anhydrous sodium sulfate). The solvent was distilled off under reduced pressure to leave an amine compound. Then, to a solution of this amine compound in ethyl acetate (50 ml) was added a saturated aqueous solution of sodium carbonate (50 ml). To the mixture was added, while vigorously stirring, chloroacetyl chloride (1.2 equivalent). After completion of the reaction, the organic layer was taken and washed with an aqueous saline solution, followed by drying (anhydrous sodium sulfate). The solvent was distilled off under reduced pressure to leave a residue (3.2 g). To a solution of this chloroacetyl compound (2.5 g, 4.35 mmol) in THF (40 ml) were added, while stirring under ice-cooling, 60% sodium hydride (3 equivalents) and methyl iodide (5 equivalents). The mixture was stirred for 5 days at room temperature. After completion of the reaction, the reaction mixture was added to an ice-cooled aqueous solution of ammonium chloride. The mixture was subjected to extraction with ethyl acetate. The extract was further dried (anhydrous sodium sulfate), then the solvent was distilled off to leave a residue. The residue was subjected to a silica gel column chromatography, eluting with n-hexane-ethyl acetate (1:1–2:3) to afford 1.9 g (80%) of the title compound as amorphous crystals, m.p.155°–157° C. (n-hexane-ethyl acetate).

$^1$H-NMR(CDCl$_3$, 200 MHz) δ: 1.08, 1.09(d,J=7 Hz,6H× 2), 1.25(d,J=7 Hz), 1.51(s,3H), 3.13(s,3H), 3.15(dd,J=12,4 Hz,1H), 3.86(s,3H), 3.95–4.25(m,3H), 4.48(ABq,2H), 6.85–7.30(m,3H) ppm. IR(KBr): 2960, 1655, 1600, 1429 cm$^{-1}$. Anal: Calcd for C$_{31}$H$_{40}$N$_2$O$_5$S; C 67.36%, H 7.29%, N 5.07% Found; C 67.44%, H 7.40%, N 5.09%.

Example 9-2

Trans-4,6,6a,8,9,10a-hexahydro-1-methoxy-7-methyl-10a-methyl-7H-indolo[3,4-gh][1,4]benzoxazine To a solution of trans-4,6,6a,7,9,10a-hexahydro-7-methyl-10a-methyl-1-methoxy-4-(2,4,6 -triisopropylphenylsulfonyl)-indolo[3,4-gh][1,4]benzoxazin-8-one (1.9 g, 3.4 mmol) in THF (30 ml) was added, while stirring under ice-cooling, LAH (3 equivalents). The mixture was heated for 3 hours under reflux. After completion of the reaction, ethanol was added to the reaction mixture, and the mixture was then added to an ice-cooled saturated aqueous solution of sodium sulfate. The mixture was subjected to extraction with ethyl acetate. The extract was washed with an aqueous saline solution, and was then dried (anhydrous sodium sulfate). The solvent was distilled off under reduced pressure. The residue was subjected to a silica gel column chromatography, eluting with ethyl acetate to leave 700 mg of a residual substance. To a solution of this residual substance in THF (10 ml) was added, at room temperature in argon streams, a solution of 0.5M naphthalene sodium in THF (10 equivalents). The mixture was stirred for 10 minutes at room temperature, and was added to an ice-cooled saturated aqueous solution of ammonium chloride, followed by extraction with ethyl acetate. The organic layer was washed with an aqueous saline solution, which was dried (anhydrous sodium sulfate). The solvent was distilled off under reduced pressure. The residue was subjected to a silica gel column chromatography, eluting with ethyl acetate to afford 250 mg (27%) of the title compound as crystals, m.p.200°–202° C. (isopropyl ether-ethyl acetate).

$^1$H-NMR(CDCl$_3$, 200 MHz) δ: 1.62(s,3H), 2.38(s,3H), 2.40–2.60(m,3H), 2.77(dd,J=11,2 Hz,1H), 3.26(m, 1H), 4.26(dt,J=12,3 Hz,1H), 6.89(d,J=9 Hz,1H), 7.15(d,J=9 Hz,1H), 7.85–8.00(br,1H) ppm. IR(KBr): 3304, 1502, 1431 cm$^{-1}$. Anal: Calcd for C$_{16}$H$_{20}$N$_2$O$_2$; C 70.56%, H 7.40%, N 10.29% Found; C 70.67%, H 7.51%, N 10.45%

Biological Test Example 1

Action of Substance-P for inhibiting biting response by its administration at subarachnoid space Five-week old male Jcl:ICR mice (10 animals per group) were employed. Dorsal cutaneous incisions were made under anesthesia at least one hour before the experiments. Substance-P (SP) was administered in an amount of 10 ng/5 μl/mouse at the subarachnoid space of the spinal cord. Then the test animals started to bite themselves at the abdomen alternately. The number of bitings was counted for one minute immediately after the SP administration. The values thus obtained were made indexes of pseudo pain reflexes caused by SP.

Test drugs were dissolved in a solution (Tween 80:ethanol:physiological saline=20:10:70) together with a given amount of SP. The solutions thus prepared were administered to test animals. In the case of oral administration, 5% suspension of gum arabica was employed, which was administered at 30 minutes before the SP administration.

The inhibition rate (%) of each sample was calculated by the following formula. Inhibition rate (%)=(number of counts in the control group–number of counts in each sample)/(number of counts in the control group)×100.

And, 50% inhibition dose (ID$_{50}$) was calculated from the primary linear regression line of dose-dependent curve.

TABLE 1

| Antagonistic action to Substance-P (Dosage 10 μg/mouse) ||
|---|---|
| Compounds (Example No.) | Inhibition rate (%) |
| 1 | 80 |
| 2 | 100 |
| 8 | 65 |

Biological Test Example 2

Acetic acid-writhing method

Male Slc:ICR mice of four-week old (10 animals per group) were employed. Test compounds were orally administered. Thirty minutes later, purified water containing 0.6% acetic acid was injected intraperitoneally (0.1 ml/10 g body weight). Writhing shown by the test animals during 20 minutes was observed on individual animals.

On each test animal, the inhibition rate against the average response times in the control group was calculated. The test compound was administered as a 5% suspension of gum arabica.

TABLE 2

| Analgesic action |||
|---|---|---|
| Compound (Example No.) | Inhibition rate (%) | Dose (mg/kg,p.o.) |
| 2 | 99 | 25 |
| 8 | 61 | 12.5 |

What is claimed is:
1. A compound of the formula

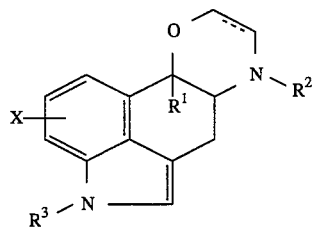

wherein X is hydrogen, lower alkyl, lower alkoxy or halogen; R$^1$ is (i) residue lower alkyl optionally substituted with halogen, (ii) lower alkenyl, (iii) lower alkynyl or (iv) aryl optionally substituted with lower alkyl, lower alkenyl, lower alkynyl, cycloalkyl, cyano, nitro, sulfonyl, amino, lower monoalkylamino, lower dialkylamino, arylamino, hydroxy, lower alkoxy, halogen, carbamoyl, carboxyl, alkylthio, aralkyl, aryl, lower alkyl carbamoyl, arylcarbamoyl, acyl, methylenedioxy, or heterocyclic ring; R$^2$ is hydrogen or lower alkyl optionally substituted by halogen, aryl, cycloalkyl, heterocyclic ring, aralkyl or acyl, wherein the aryl and heterocyclic ring may be substituted on the lower alkyl through an oxygen, sulfur or nitrogen atom; R$^3$ is hydrogen, lower alkyl optionally substituted by halogen, or arylsulfonyl optionally substituted by lower alkyl; and ----- shows a single bond or a double bond, or a pharmacologically acceptable acid addition salt thereof.

2. A compound according to claim 1, wherein X is hydrogen or C$_{1-6}$ alkoxy.

3. A compound according to claim 1, wherein R$^1$ is C$_{1-6}$ alkyl, C$_{2-6}$ alkenyl or phenyl.

4. A compound according to claim 1, wherein R$^2$ is hydrogen, C$_{1-6}$ alkyl or a group of the formula: —(CH$_2$)$_n$AR$^4$ (wherein n is integer of 1 to 6; A is a bond or oxygen, sulfur or nitrogen atom; R$^4$ is hydrogen, phenyl, 1-phthalimidyl, or 4-benzylpiperadyl).

5. A compound according to claim 1, wherein R$^3$ is hydrogen or sulfonyl which may be substituted by C$_{1-6}$ alkyl, phenyl or tolyl.

6. A compound according to claim 1, wherein X is hydrogen or C$_{1-3}$ alkoxy; R$^1$ is C$_{1-3}$ alkyl, vinyl or phenyl; R$^2$ is hydrogen, C$_{1-6}$ alkyl or a group of the formula: —(CH$_2$)$_n$AR$^4$, wherein n is 1 to 6; A is a bond or O, S, or N; R$^4$is hydrogen, phenyl, 1-phthalimidyl, or 4-benzylpiperadyl; R$^3$ is hydrogen or triisopropylbenzenesulfonyl; and ----- is a single bond.

7. A compound according to claim 1, which is trans-4,6,6a,8,9,10a-hexahydro-7-ethyl-10a-vinyl-7H-indole[3,4-gh][1.4]benzoxazine.

8. A compound according to claim 1, which is trans-4,6,6a,8,9,10a-hexahydro-7-ethyl-1-methoxy-10a-methyl- 10a-methyl-7H-indole[3,4-gh][1.4]benzoxazine.

9. A compound according to claim 1, which is trans-4,6,6a,8,9,10a-hexahydro-7-ethyl-10a-methyl-7H-indolo[3,4-gh][1.4]benzoxazine fumalate.

10. A pharmaceutical composition which contains the compound according to claim 1 together with a pharmaceutically acceptable carrier, vehicle or diluent.

11. A method for prophylaxis or treatment of a mammal suffering from pain, which comprises administering to said mammal an effective amount of the compound according to claim 1.

* * * * *

UNITED STATES PATENT AND TRADEMARK OFFICE
CERTIFICATE OF CORRECTION

PATENT NO. : 5,466,689
DATED : November 14, 1995
INVENTOR(S) : KANEYOSHI KATO; TAKAYUKI DOI and MITSUO YAMAMOTO It is certified that error appears in the above-indentified patent and that said Letters Patent is hereby corrected as shown below:

On the Title page, item [19] immediately under "United States Patent" change "Yamamoto et al." to —Kato et al.—; in the left hand column, section "[75] Inventors:" should read —Kaneyoshi Kato, Hyogo; Takayuki Doi; Mitsuo Yamamoto, both of Osaka, all of Japan—.

In column 24 (in claim 1), at line 33, delete "residue".

Signed and Sealed this

Nineteenth Day of March, 1996

Attest:

BRUCE LEHMAN

Attesting Officer

Commissioner of Patents and Trademarks